US010656108B2

(12) United States Patent
Csutak

(10) Patent No.: US 10,656,108 B2
(45) Date of Patent: May 19, 2020

(54) MEASURING SOURCE ROCK POTENTIAL USING A QUANTUM ELECTRONIC SCANNER

(71) Applicant: Saudi Arabian Oil Company, Dhahran (SA)

(72) Inventor: Sebastian Csutak, Houston, TX (US)

(73) Assignee: Saudi Arabian Oil Company, Dhahran (SA)

( * ) Notice: Subject to any disclaimer, the term of this patent is extended or adjusted under 35 U.S.C. 154(b) by 126 days.

(21) Appl. No.: 15/852,324

(22) Filed: Dec. 22, 2017

(65) Prior Publication Data

US 2019/0195816 A1  Jun. 27, 2019

(51) Int. Cl.
| | | |
|---|---|---|
| *G01N 24/08* | (2006.01) | |
| *G01N 33/24* | (2006.01) | |
| *G01V 3/14* | (2006.01) | |
| *E21B 49/00* | (2006.01) | |
| *E21B 43/26* | (2006.01) | |
| *E21B 49/08* | (2006.01) | |
| *E21B 21/06* | (2006.01) | |
| *G01V 3/32* | (2006.01) | |

(52) U.S. Cl.
CPC ......... *G01N 24/081* (2013.01); *E21B 21/066* (2013.01); *E21B 43/26* (2013.01); *E21B 49/005* (2013.01); *E21B 49/088* (2013.01); *G01N 33/241* (2013.01); *G01V 3/14* (2013.01); *G01V 3/32* (2013.01)

(58) Field of Classification Search
CPC .. G01N 24/081; G01N 33/241; E21B 21/066; E21B 43/26; E21B 49/005; E21B 49/088; G01V 3/14

USPC .......................................................... 324/303
See application file for complete search history.

(56) References Cited

U.S. PATENT DOCUMENTS

| | | | | |
|---|---|---|---|---|
| 3,649,201 A | * | 3/1972 | Scalan | G01N 33/241 436/27 |
| 3,740,641 A | | 6/1973 | Hwang et al. | |
| 4,560,663 A | | 12/1985 | Nicksic et al. | |
| 5,945,867 A | * | 8/1999 | Uda | H03K 17/693 327/389 |

(Continued)

FOREIGN PATENT DOCUMENTS

| | | |
|---|---|---|
| WO | 2015048249 | 4/2015 |
| WO | 2015088566 | 6/2015 |

OTHER PUBLICATIONS

International Search Report and Written Opinion issued in International Application No. PCT/US2018/066173 dated Mar. 22, 2019, 15 pages.

*Primary Examiner* — Melissa J Koval
*Assistant Examiner* — Rahul Maini
(74) *Attorney, Agent, or Firm* — Fish & Richardson

(57) ABSTRACT

The present disclosure describes methods and systems for determining source rock potential in a subterranean region of a hydrocarbon reservoir. One method includes receiving, an electron spin resonance (ESR) image from an in-situ ESR scanner that is attached to a wellbore at a first subterranean location, wherein the wellbore extends into the subterranean region of the hydrocarbon reservoir; determining, a spin concentration level of a source rock in the first subterranean location based on the ESR image; and determining, the source rock potential at the first subterranean location based on the determined spin concentration level.

20 Claims, 7 Drawing Sheets

(56) References Cited

U.S. PATENT DOCUMENTS

| | | | | |
|---|---|---|---|---|
| 6,573,715 | B2* | 6/2003 | King | G01V 3/32 |
| | | | | 324/300 |
| 8,967,249 | B2 | 3/2015 | Akkurt et al. | |
| 9,086,359 | B2 | 7/2015 | Wiley, Sr. | |
| 10,082,594 | B2* | 9/2018 | Ramirez | G01V 3/32 |
| 2001/0028247 | A1 | 10/2001 | King et al. | |
| 2010/0105975 | A1* | 4/2010 | Baird | E21B 43/2403 |
| | | | | 166/247 |
| 2014/0035578 | A1* | 2/2014 | Song | G01V 3/32 |
| | | | | 324/309 |
| 2016/0054412 | A1* | 2/2016 | Ganssle | G01V 3/32 |
| | | | | 324/309 |

* cited by examiner

MEASURING SOURCE ROCK POTENTIAL USING A QUANTUM ELECTRONIC SCANNER

TECHNICAL FIELD

This disclosure relates to measuring source rock potential using a quantum electronic scanner.

BACKGROUND

In the hydrocarbon production industry, a source rock refers to a rock that is capable of generating or that has generated movable quantities of hydrocarbons. The potential of the source rock refers to the amount of hydrocarbons that may be produced by the source rock. An area may be identified as a reservoir if the area has source rocks that contain organic matter in sufficient quantity to generate and expel hydrocarbons. Measuring source rock potential before and during the exploration and production processes of a reservoir can help to determine the productivity of the reservoir, plan drilling and extraction operations, and maintain the life cycle of the reservoir.

SUMMARY

The present disclosure describes methods and systems for measuring source rock potential using a quantum electronic scanner. One method includes receiving, an electron spin resonance (ESR) image from an in-situ ESR scanner that is attached to a wellbore at a first subterranean location, wherein the wellbore extends into the subterranean region of the hydrocarbon reservoir; determining, a spin concentration level of a source rock in the first subterranean location based on the ESR image; and determining, the source rock potential at the first subterranean location based on the determined spin concentration level.

The details of one or more implementations of the subject matter of this disclosure are set forth in the accompanying drawings and the description. Other features, aspects, and advantages of the subject matter will become apparent from the description, the drawings, and the claims.

DESCRIPTION OF DRAWINGS

Like reference numbers and designations in the various drawings indicate like elements.

DETAILED DESCRIPTION

Figure 1:
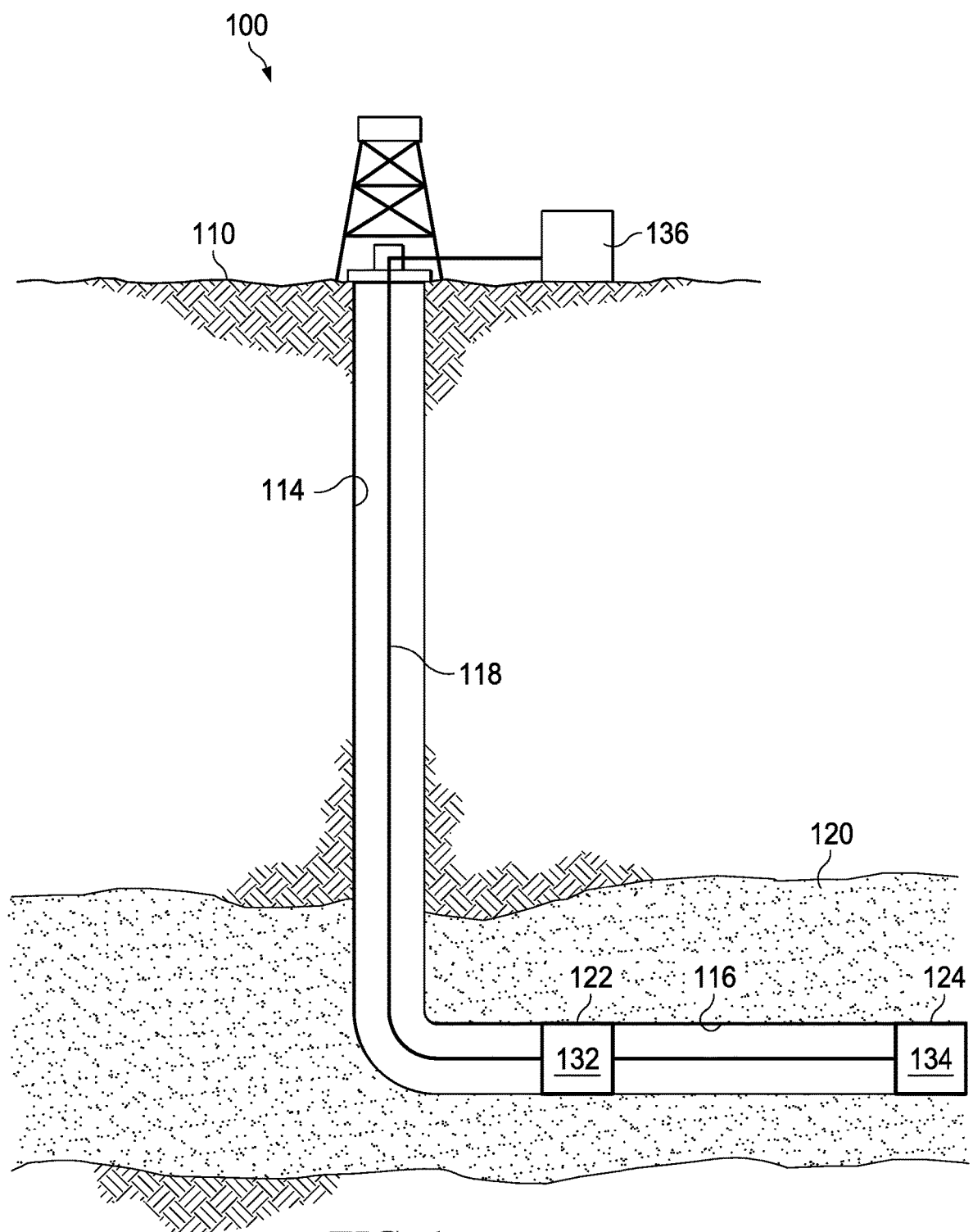
FIG. 1 is a schematic diagram that illustrates an example well system, according to an implementation.

This disclosure generally describes methods and systems for measuring source rock potential using a quantum electronic scanner. In some implementations, the source rock potential can be measured using a spectroscopic technique called electron spin resonance (ESR). In some cases, ESR is also referred to as electron paramagnetic resonance (EPR). ESR is based on the process of resonant absorption of microwave radiation by paramagnetic species in the presence of a magnetic field.

An electron in an atom has an intrinsic angular momentum. This angular momentum may have quantized values and can be assigned specific quantum numbers. A paramagnetic atom has one or more unpaired electron spins and an angular momentum J=L+S that is not equal to zero, where L is the orbital angular momentum and the S is the spin angular momentum. When a paramagnetic specimen is placed in a magnetic field, the one or more unpaired electrons distribute themselves between low and high energy states.

The energy differences measured in EPR spectroscopy are predominately due to the interaction of unpaired electrons in the sample with the magnetic field produced by the magnet. This effect is called the Zeeman Effect. Assuming that the spin quantum number s=½, and magnetic components $m_s$=+½ or $m_s$=−½, the magnetic field has a strength of $B_0$, the g-factor of the electron is $g_e$, where $g_e$=2.0023192778 for free electron, and $u_B$ is the Bohr magneton. The energy due to the Zeeman effect can be represented as:

$$E = m_s g_e u_B B_0 \qquad (1)$$

Thus the separation between the lower and upper state is $g_e u_B B_0$. Accordingly, the separation of the energy level is proportional to the magnetic field's strength.

The Zeeman effect removes the degeneracy of the energy levels. However, other interactions, for example, the environment and field seen by the unpaired electrons, can modify the energy levels. Organic free radicals, with only hydrogen (H), oxygen (O), carbon (C), and nitrogen (N) atoms, will have a small contribution from spin-orbit coupling, producing g-factors very close to $g_e$. On the other hand, g-factors of much larger elements, such as metals, may be significantly different from $g_e$. Therefore, the value of a g-factor can be taken as a fingerprint of the molecule, and EPR can be used to identify components in the source rock.

Free radicals help promote the cleaving of bonds in kerogen to produce bitumen which eventually produces oil and gas. There are many types found in kerogen, including for example: sulfur (S), vanadium (V), nickel (Ni), iron (Fe), cobalt (Co), and manganese (Mn). V and Ni for example are complexed within porphyrin organic molecules. The relative abundance of the porphyrin organic molecules can be used to determine whether the kerogen composing source rocks formed under anoxic conditions or more oxidizing conditions. An increasing amount of the abundance of Sulphur in koregen indicates an increasing likelihood of the presence of low activation energy, and thus an increasing likelihood that the source rock may have undergone categenesis at a low burial temperature. The Fe free radical in source rocks can be associated with pyrite. Framboids and smaller euhedral crystals strongly associated with the kerogen can indicate that pyrite can be a substrate for catalyzing reactions during the maturation process. Moreover, the variation in Fe in other lithologies can also be a signal of changing redox conditions.

Accordingly, one can follow the abundance of some free radicals as a function of maturity. In some cases, sample free radical spin concentration of several rock sources with several maturity ranges can be determined. The free radical spin concentration can increase from the lower level, indicating immaturity, upward to a highest concentration, indicating a late oil window, and then decline, indicating that the metagenesis stage of gas maturity is reached. The point where free radical concentrations start to decline can indicate a depletion in generative potential of kerogen and a decrease in the ability form hydrocarbons.

EPR provides a non-destructive method for analyzing the source rock for assessing maturity, from both natural transformation and artificial transformation induced by pyrolysis. Moreover, EPR can also be used for assessing the depositional environment using the free radicals discussed. With respect to the depositional environment, in kerogen that has been deposited under anoxic conditions, V free radicals are greater in abundance than Ni. In kerogen that has been deposited more oxidizing conditions, V free radicals are less in abundance than Ni. With the increasing of V under anoxic conditions, S will also increase in the kerogen. In addition, Mn in carbonate source rocks is often associated with the tests of biogeneic sources, in particular coccoliths that have been deposited in anoxic conditions. The decreasing concentration or absence of concentration of Mn can indicate that more oxidizing conditions were prevalent during the carbonate deposition.

Additionally, the isotope fractionation with maturity will lead to an enrichment of carbon-13 (13C) over that of carbon-12 (12C). Thus, maturity of kerogen can also be determined by comparing the concentration level of 13C versus 12C. Carbonates also change the level concentration of 13C according to the signature of the isotope precipitated from the surface water. For the carbonate rocks that are composed of allochems, which represent the remnants of organisms that precipitated their shells in isotopic equilibrium with the ocean surface water, the 13C signature can be used to monitor the organic productivity of surface waters or the increase in global carbon burial. In addition, the marked depletion in 13C can indicate dolomitization and other diagenetic processes. This can be used in chemostratigraphy studies applied to carbonate reservoirs.

In some cases, instead of extracting samples from a well and analyzing the samples in a lab, ESR device can be miniaturized and placed in a borehole for in-situ measurements. The in-situ ESR device can be attached to the outside of a wellbore that extends downward into the subterranean region of a reservoir. The in-situ ESR device can also be referred to as the in-situ ESR scanner or the in-situ ESR scanning device. The in-situ ESR device can include one or more low-foot-print microwave transmitters and receivers that are constructed using semiconductor components such as silicon-germanium (SiGe), complementary metal-oxide-semiconductor (CMOS), indium phosphide (InP), or gallium arsenide (GaAs). By using these semiconductor components, the in-situ ESR device can sustain the high temperature operating environment of a borehole. FIGS. 1-8 and associated descriptions provide additional details of these implementations.

Using the in-situ ESR device to perform measurement in a borehole can provide one or more advantages. For example, the measurement results can be processed in real-time to provide assessment of source rock potential to the operating crews in the field, and therefore reduce the turn-around time and improves efficiency. In addition, the in-situ ESR device may be easier to transport and install, and therefore reduce the operating expenses incurred by transporting and maintaining bulky ESR devices in the field. Moreover, in some cases, a borehole may stretch over a long distance in the subterranean region. In these or other cases, multiple in-situ ESR devices can be placed in different locations of the borehole. By receiving and analyzing images of these different in-situ ESR devices, source rock potentials at each respective location can be determined. Other advantages will be apparent to those of ordinary skill in the art.

FIG. 1 is a schematic diagram that illustrates an example well system 100, according to an implementation. The example well system 100 can use in-situ ESR scanners to generate ESR images for rock samples around a wellbore at a subterranean location, as will be described subsequently.

The example well system 100 includes a wellbore 114 extending below the terranean surface 110. The wellbore 114 includes a portion 116 that extends into source rock region 120 in the subterranean area of a reservoir. In some cases, as shown in FIG. 1, the wellbore portion 116 can be positioned horizontally. For example, the wellbore portion 116 can be positioned in parallel to the horizon of the terranean surface 110. In some cases, the wellbore portion 116 can extend to several kilometers.

The well system 100 also includes in-situ ESR scanners 132 and 134 that are attached to the wellbore 114. The in-situ ESR scanners 132 and 134 can generate magnetic fields, irradiate microwaves or other electronic magnetic (EM) waves, and generate ESR images. The in-situ ESR scanners 132 and 134 can transmit the ESR images to a master device 136 for analysis. In some implementations, one in-situ ESR scanner can be attached to each wellbore. Alternatively or in combination, more than one in-situ ESR scanner can be attached to each wellbore. For example, as shown in FIG. 1, the in-situ ESR scanners 132 and 134 are attached at different locations (locations 122 and 124, respectively) of the wellbore portion 116. Therefore, each of the in-situ ESR scanners 132 and 134 can transmit ESR images for rocks at the respective locations. In some cases, the in-situ ESR scanners 132 and 134 can transmit an identification of the respective in-situ ESR scanner with the ESR images generated by the respective in-situ ESR scanner. This approach can help the master device 136 to identify ESR images generated at different subterranean locations, and determine the source rock potentials at each subterranean location. FIGS. 2-8 and associated descriptions provide additional details of the operations of the in-situ ESR scanners.

The well system 100 also includes the master device 136. The master device 136 represents a computing device that is configured to receive ESR images from the in-situ ESR scanners 132 and 134, and analyze the ESR images to determine source rock potentials at the subterranean locations 122 and 124, respectively.

In some cases, the master device 136 and the in-situ ESR scanners 132 and 134 can communicate using wireline communication technologies. For example, as shown in FIG. 1, the master device 136 and the in-situ ESR scanners 132 and 134 can be connected by a cable 118. The in-situ ESR scanners 132 and 134 can use the cable 118 to transmit ESR images to the master device 136. The in-situ ESR scanners 132 and 134 can also use the cable 118 to receive commands from the master device 136.

In operation, the in-situ ESR scanners 132 and 134 generate magnetic fields, irradiate the microwaves on rocks at the locations 122 and 124, or on rock samples collected from the rocks at the locations 122 and 124, and generate ESR images. The in-situ ESR scanners 132 and 134 transmit the ESR images to the master device 136. The master device 136 analyzes the ESR images and determines source rock potentials at the locations 122 and 124. FIGS. 2-8 and associated descriptions provide additional details of these implementations.

Figure 2:
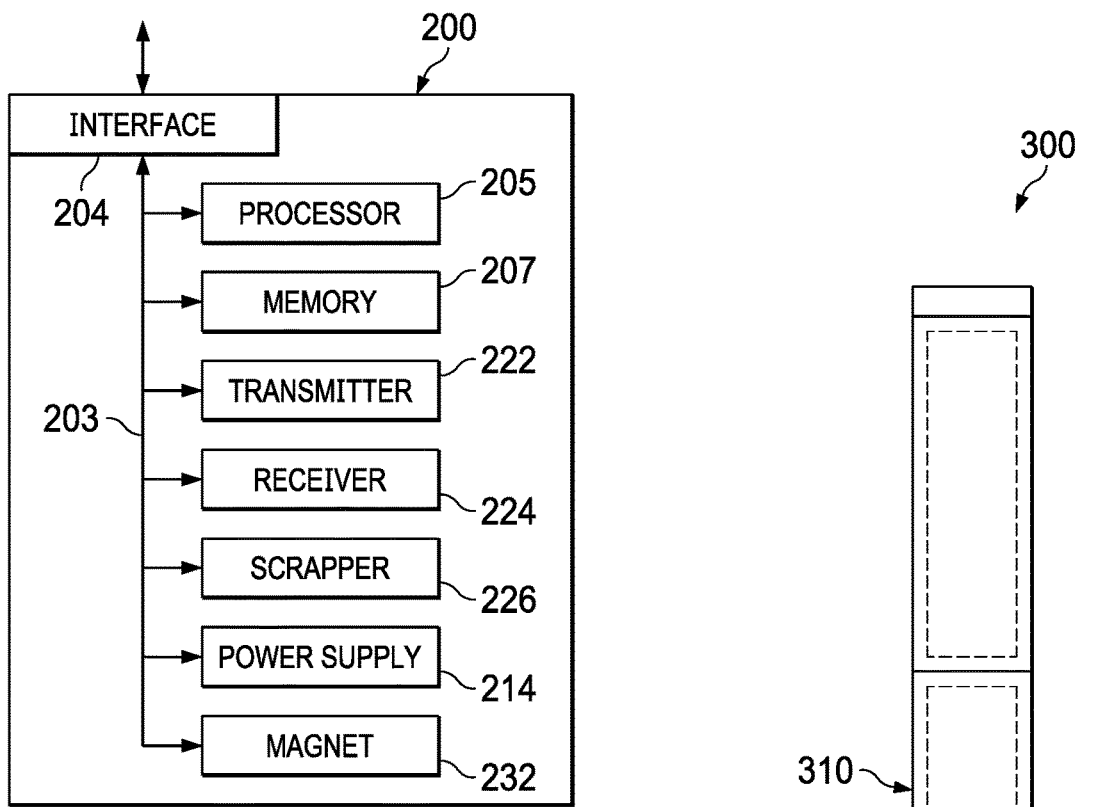
FIG. 2 is a block diagram of an example in-situ electron spin resonance (ESR) scanner used to measure source rock potential, according to an implementation.

FIG. 2 is a block diagram of an example in-situ ESR scanner 200 used to measure source rock potential, according to an implementation. At a high level, the in-situ ESR scanner 200 includes an interface 204, a processor 205, a memory 207, a system bus 203, a power supply 214, a transmitter 222, a receiver 224, a scratcher 226, and a magnet 232. An in-situ ESR device may include additional, different, or fewer components as shown in FIG. 2, as appropriate.

Figure 3:
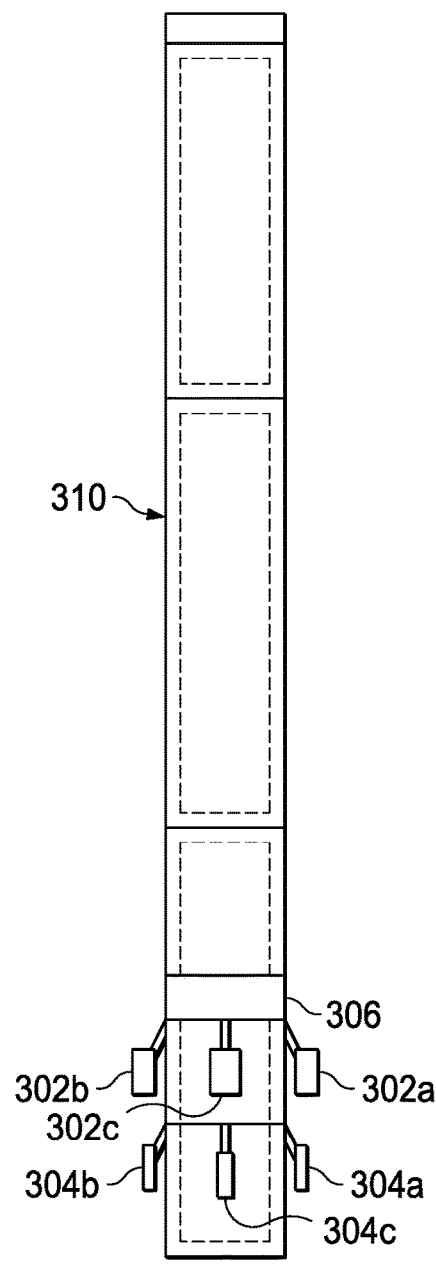
FIG. 3 is a schematic diagram that illustrates an example installation scenario of the in-situ ESR scanner, according to an implementation.

In some cases, the example in-situ ESR scanner 200, or components of the example in-situ ESR scanner 200 can be packaged in a protective case or a pad. The protective case or pad can be constructed using metal, plastic, or any other materials that prevent the scanner 200 or components of the scanner 200 from sustaining damages caused in the subterranean environment. The protective case or pad can also provide good contact with the rock formations around the wellbore and reduce losses in water and air. In some cases, some components, for example, the transmitter 222, the receiver 224, the scratcher 226, or any combinations thereof can be placed outside of the scanner 200. FIG. 3 and associated descriptions provide additional details of these implementations.

Figure 7A:
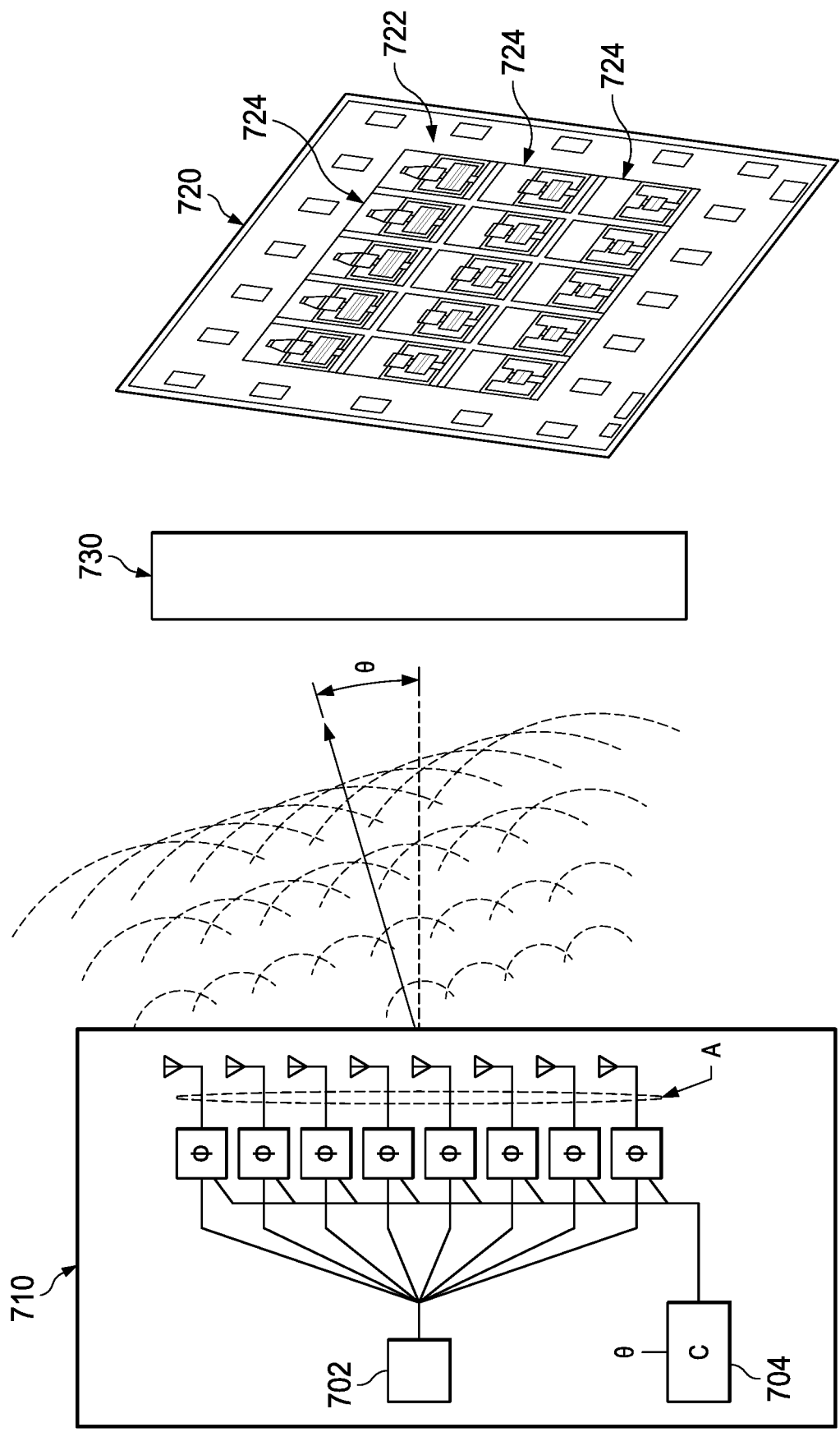
FIG. 7A illustrates an example ESR measurement in a transmission configuration, according to an implementation.
Figure 7B:
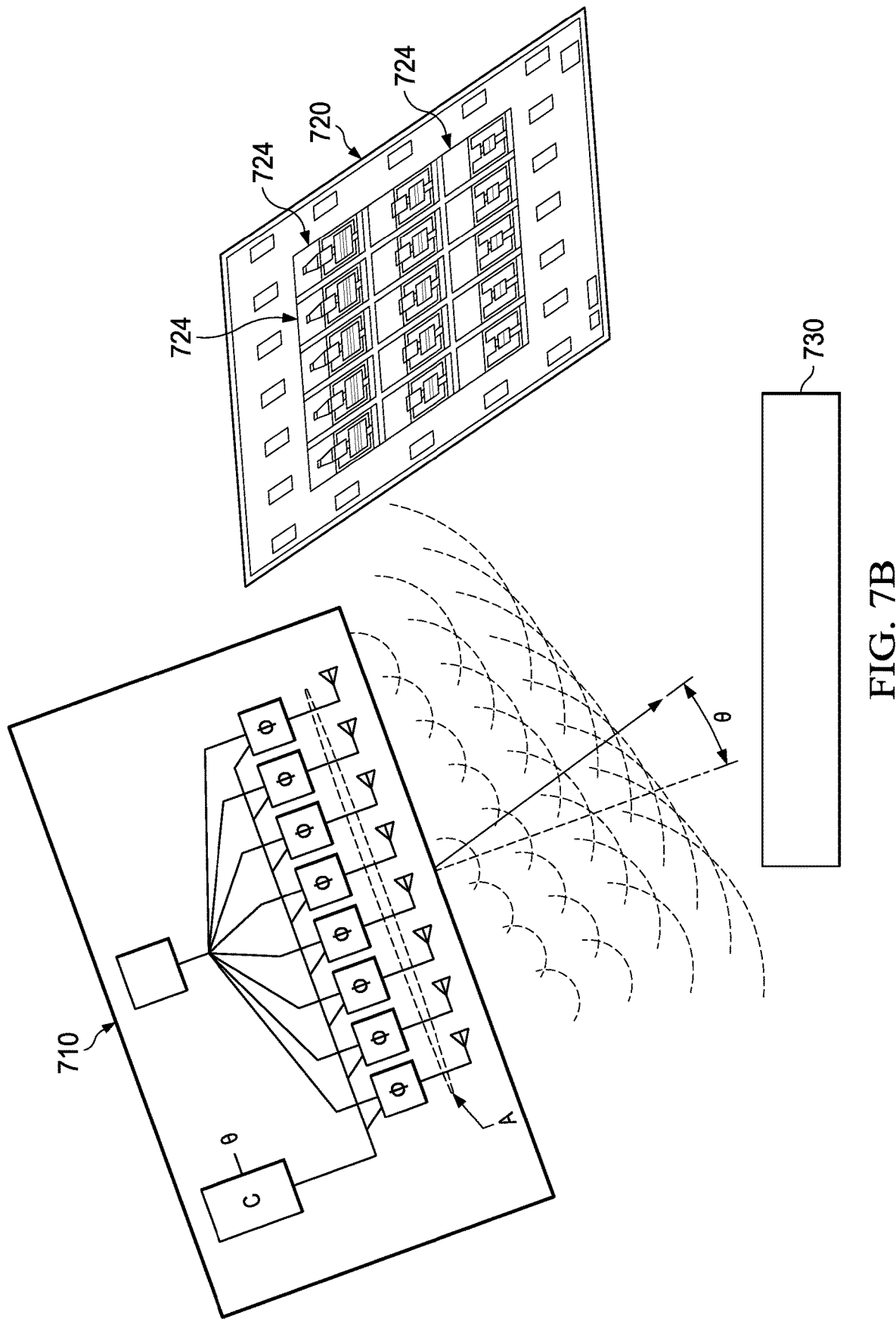
FIG. 7B illustrates an example ESR measurement in a reflection configuration, according to an implementation.

The transmitter 222 generates EM waves to radiate onto the rock samples. In some implementations, the transmitter 222 can be constructed using field effect transistors. FIGS. 7A and 7B and associated descriptions provide additional details of these implementations. The receiver 224 generates images based on the EM waves that are reflected or penetrated through the rock samples. In some implementations, the receiver 224 can be constructed using CMOS. FIGS. 7A and 7B and associated descriptions provide additional details of these implementations.

The transmitter 222 generates EM waves to radiate onto the rock samples. The receiver 224 generates images based on the EM waves that are reflected or penetrated through the rock samples. The transmitter 222 and the receiver 224 can be placed in a transmission configuration, where the EM waves penetrate through the rock samples, or in a reflection configuration, where the EM waves reflect from the rock samples. FIGS. 7A and 7B and associated descriptions provide additional details of these implementations.

The transmitter 222 and the receiver 224 can be constructed using semiconductor components such radio frequency complementary metal-oxide-semiconductor (RFCMOS), silicon-germanium (SiGe), indium phosphide (InP), or gallium arsenide (GaAs). Comparing to conventional semiconductors, these transistors can operate at higher temperature, and thus are suitable for in-situ operation. In some implementations, the breakdown voltage for GaA or SiGe components can be modified by changing the bandgap structure of these components, which can reduce the current leakage and make these component more suitable for operating in a high temperature environment.

In some cases, the transmitter 222 can generate microwaves to irradiate on the rock samples. Microwave can be used to reduce the strength of the magnetic field required for the ESR measurements. For example, the microwaves can be in X band, at frequency of about 7.0 to 11.2 gigahertz (GHz). The microwaves can also be in L band, at frequency of about 1 to 2 GHz, or other bands. In some cases, magnetic field of about 3000 gausses may be used to generate ESR images if X band microwaves are used, while magnetic field of about 300 gausses can be used to generated ESR images if L band microwaves are used. Using microwaves at L band can also provide signals that are less attenuated in H2O, which may be present at the well site or inside the wellbore.

The scratcher 226 can be configured to scratch the surface of the rock samples. By scratching mud or other borehole fluids from the rock sample, the contamination in the measured signal can be reduced. In some cases, the scratcher 226 can also include components that can be used to take rock samples from the rock formation around the borehole. For example, the scratcher 226 can include an arm that extends outside of the scanner 200 to reach to the rock. The scratcher 226 can also include a claw at the front end of the arm that can scratch the rock surface to make them loose. In some cases, the scratcher 226 can include a collector that collects the loose rock sample, and the transmitter 222 can direct the EM wave to the collected rack sample. In some implementations, instead of taking rock samples for measurement, the transmitter 222 can direct the EM wave to the rock surface around the borehole and the receiver 224 can generate images based on EM wave that is reflected from the rock surface.

The scanner 200 also includes the magnet 232. Although illustrated as a single magnet 232 in FIG. 2, two or more magnets 232 may be used according to particular needs, desires, or particular implementations of the scanner 200. The magnet 232 can produce magnetic field that is strong enough for ESR measurement. The magnet 232 can be constructed using magnetized materials. Alternatively or additionally, the magnet 232 can be constructed using electromagnets.

Each of the components of the scanner 200 can communicate using the system bus 203. In some implementations, any or all of the components of the scanner 200, hardware or software (or a combination of both hardware and software), may interface with each other or the interface 204 (or a combination of both), over the system bus 203, using standardized or proprietary protocols.

The scanner 200 includes the interface 204. Although illustrated as a single interface 204 in FIG. 2, two or more interfaces 204 may be used according to particular needs, desires, or particular implementations of the scanner 200. The interface 204 is used by the scanner 200 for communicating with other systems that are connected to the scanner 200. For example, the interface 204 may be used to communicate with a master device operating on the surface of the reservoir. The scanner 200 can use the interface 204 to transmit the images generated by the receiver 224 to the master device. The scanner 200 can also use the interface 204 to receive commands from the master device.

Generally, the interface 204 comprises logic encoded in software or hardware (or a combination of software and hardware). More specifically, the interface 204 may comprise software supporting one or more communication protocols associated with communications such that the scanner 200 and is operable to communicate physical signals within and outside of the illustrated scanner 200. The interface 204 can be configured to support wireline or wireless communication protocols that connect the scanner 200 with the master device. For example, the scanner 200 can be connected to the master device using a coaxial cable, an optical cable, a twisted pair, or other wireline communication technologies. Alternatively, the scanner 200 can be connected to the master device using EM waves or other wireless communication technologies.

The scanner 200 includes a processor 205. Although illustrated as a single processor 205 in FIG. 2, two or more processors may be used according to particular needs, desires, or particular implementations of the scanner 200. Generally, the processor 205 executes instructions and manipulates data to perform the operations of the scanner 200 and any algorithms, methods, functions, processes, flows, and procedures, as described in the instant disclosure. For example, the processor 205 can be configured to control the transmitter 222 to generate EM waves and radiate on the rock samples or rock surface around the borehole. The processor 205 can also be configured to form a signal that includes the generated images from the receiver 224 and instruct the interface 204 to transmit the generated images to the master device. The processor 205 can also be configured to control the operations of the scratcher 226.

The scanner 200 also includes a memory 207 that can hold data for the scanner 200. For example, memory 207 can be random access memory (RAM), read only memory (ROM), optical, magnetic, and the like, storing data consistent with this disclosure. In some implementations, memory 207 can be a combination of two or more different types of memory (for example, a combination of RAM and magnetic storage) according to particular needs, desires, or particular implementations of the scanner 200 and the described functionality. Although illustrated as a single memory 207 in FIG. 2, two or more memories 207 (of the same or a combination of types) can be used according to particular needs, desires, or particular implementations of the scanner 200 and the described functionality.

The scanner 200 can also include the power supply 214. The power supply 214 can include a rechargeable or non-rechargeable battery that can be configured to be either user- or non-user-replaceable. In some implementations, the power supply 214 can include power-conversion or management circuits (including recharging, standby, or other power management functionality).

FIG. 3 is a schematic diagram 300 that illustrates an example installation scenario of the in-situ ESR scanner, according to an implementation. The diagram 300 includes a wellbore 310 that is located in the subterranean region of a reservoir. The wellbore 310 is surrounded by rocks. The in-situ ESR scanner 306 is attached to the wellbore 310. In some cases, as shown in FIG. 3, the in-situ ESR scanner 306 is placed outside of the wellbore 310. Alternatively, the ESR scanner 306 can be placed inside of the wellbore 310. The ESR scanner 306 is connected to transmitters 302a, 302b, and 302c, and receivers 304a, 304b, and 304c. The transmitters 302a-c and receivers 304a-c are attached to the outside of the wellbore 310. In one implementation, the in-situ ESR scanner 306 and each of the transmitters and receivers can be placed in a pad that is attached to the outside of the wellbore 310. The pad can be constructed using non-conductive dielectric materials such as Plastics Environmental Council (PEC) plastic, carbon fiber, or high density polyethylene materials. Each transmitter corresponds to a respective receiver. For example, the transmitter 302a corresponds to the receiver 304a. In some cases, one set of transmitter and receiver is placed at one location of the wellbore 310. Alternatively, as shown in FIG. 3, multiple sets can be placed at one location of the wellbore 310, while each set is placed at a different side of the wellbore 310.

In operation, the transmitters 302a-c can generate EM waves and irradiate onto the rock surface around the wellbore 310. The receivers 304a-c can receive the reflected wave and generate images based on the reflected wave. In some cases, a scratcher can scratch rock samples from the rock surface and the transmitters 302a-c can direct the microwave towards the rock samples. The ESR scanner 306 can transmit the generated images to the master device on the surface.

Figure 4:
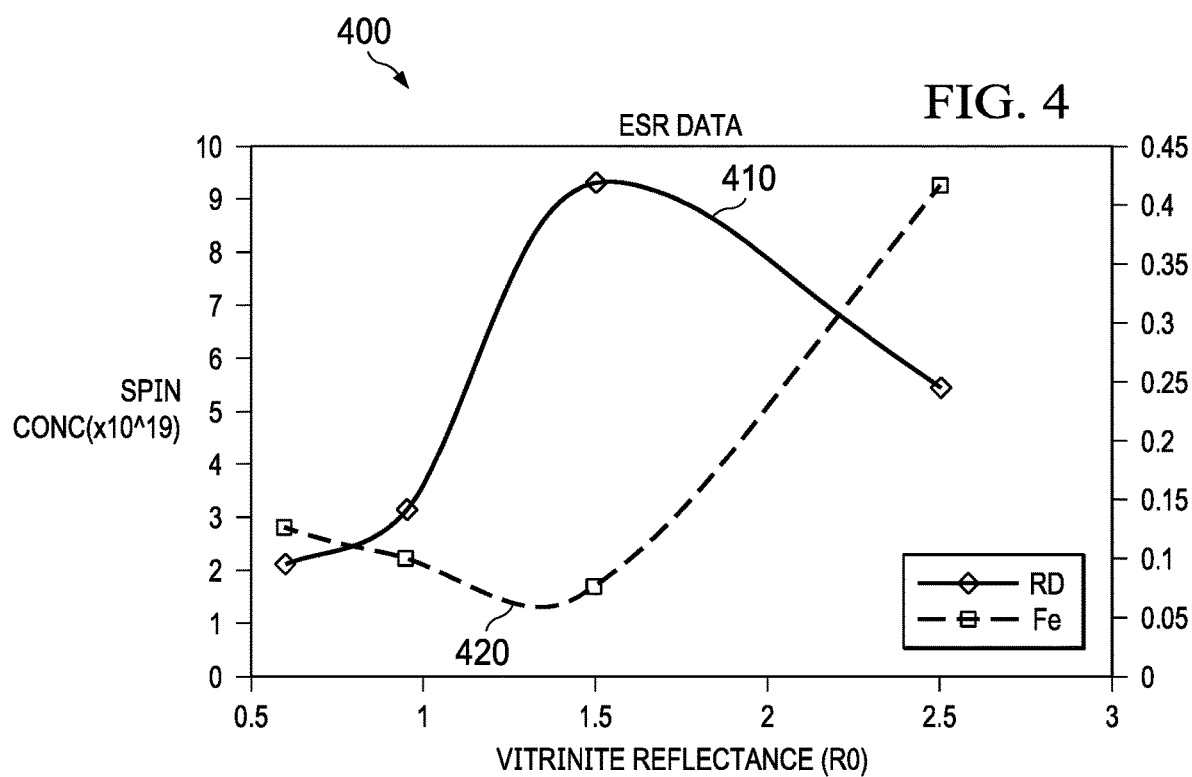
FIG. 4 is a chart illustrating example ESR measurements, according to an implementation.

FIG. 4 is a chart 400 illustrating example ESR measurements, according to an implementation. As illustrated, the spin concentration level has a parabolic dependence on the vitrine reflectance. The chart 400 includes curve 410, which shows the spin concentration level of free radicals measured against vitrine reflectance, and curve 420, which shows the spin concentration level of Fe measured against vitrine reflectance. For more mature samples, the spin concentration level would increase for free radicals and decrease for iron. Therefore, the spin concentration level of a source rock sample can be used to estimate the maturity of the source rock sample.

Figure 5:
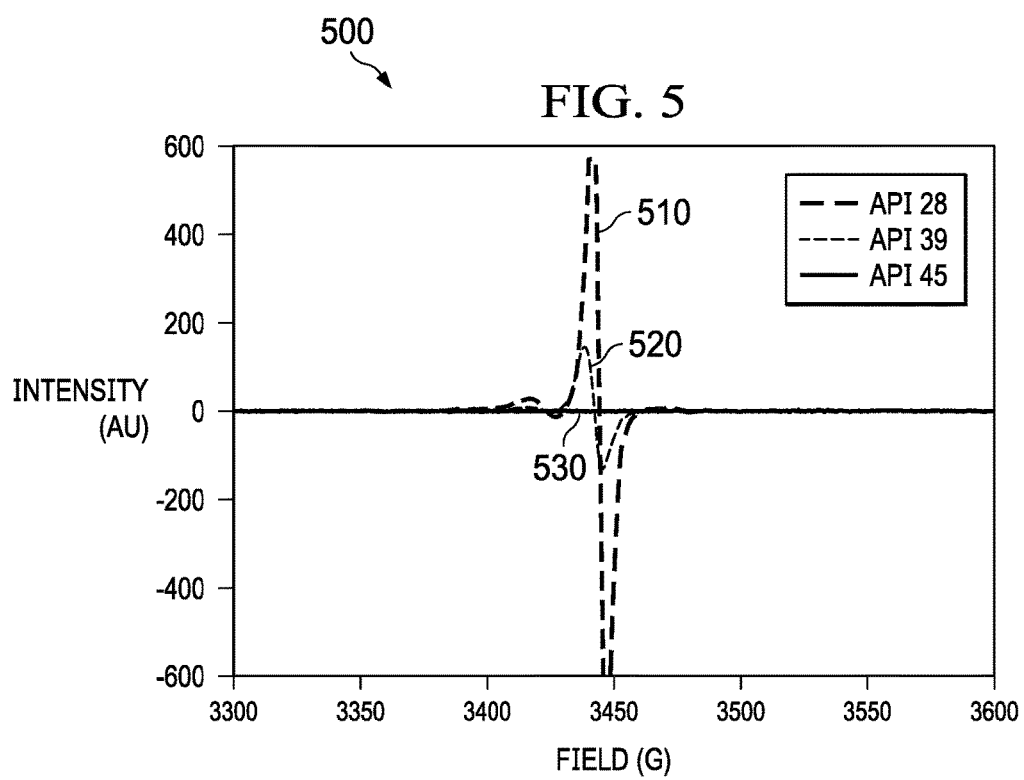
FIG. 5 is a chart illustrating example ESR measurements for spin concentration levels, according to an implementation.

FIG. 5 is a chart 500 illustrating example ESR measurements for spin concentration levels, according to an implementation. As illustrated, samples with different maturity can present different spin concentration levels (represented in intensity measurements) when measured under different magnetic field strengths. The chart 500 includes curves 510, 520, and 530, representing the measurement of oil samples with API 25, API 39, and API 46, respectively. As shown in chart 500, API 25 has a much higher peak in spin concentration levels than API 39 and API 46. The spin concentration is proportional with the stable radicals present in the asphaltenes. Lighter crude may have a low spin concentration, and present a low ESR signals. The Vanadyl peaks are proportional with the vanadium porphyrin, which is a result of the Magnesium (Mg) porphyrin degradation during the maturation process. Therefore, the Vanadyl peaks are indicators of the reduction-oxidation reaction (REDOX) conditions in the basin.

Figure 6:
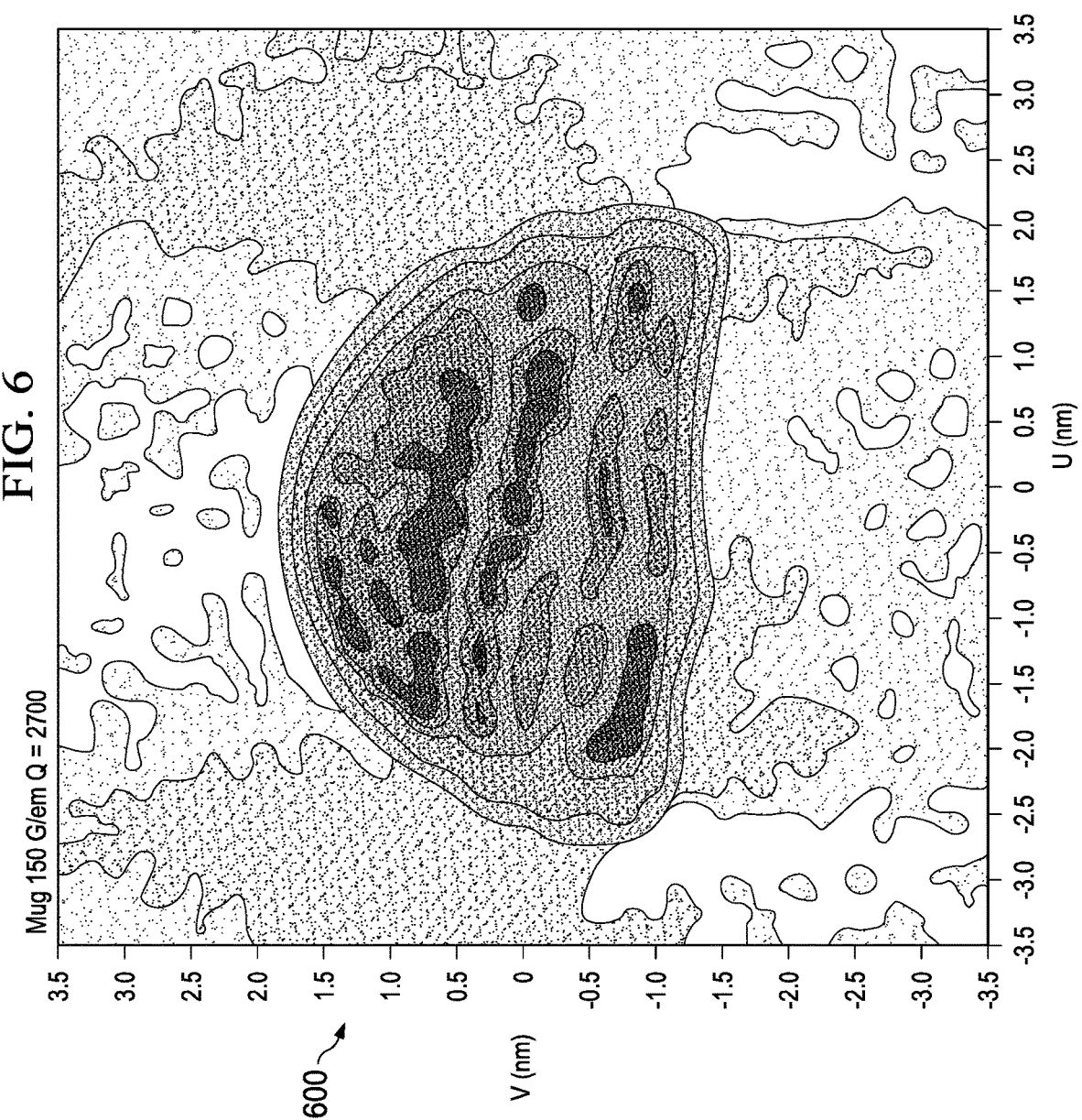
FIG. 6 is an example ESR image, according to an implementation

FIG. 6 is an example ESR image 600 for a sample that is 6 mm in diameter, according to an implementation. The image 600 was obtained in a transmission configuration measurement. Similar images can be obtained using a reflection configuration. As discussed previously, the image 600 is rendered based on a plurality of intensity values of received signals scanned from the sample. Each intensity value represents the intensity level of the EM waves received at a particular location. The bar 610 represents the scale for the intensity levels, which ranges from −0.7 to 3.2 kilo arbitrary units (Kau). The intensity levels in the image 600 indicate the spin concentration distribution of the sample. By correlating the images with a database that includes different spin concentration levels for different maturity samples, the maturity of the measured sample can be determined.

FIG. 7A and FIG. 7B illustrate example ESR measurement configurations, according to respective implementations. FIG. 7A illustrates an example irradiation operation in a transmission configuration, according to an implementation. FIG. 7A includes a transmitter 710 and a receiver 720 that can be used for in-situ operations described previously.

The transmitter 710 includes a transmitting circuit 702 and a controller 704. The transmitting circuit 702 includes one or more transistors that are configured to generate EM waves towards the sample 730. The EM waves can be microwaves, for example, in X band or L band. In some implementations, the one or more transistors can form radio frequency (RF) components such as a filter, mixer, oscillator, switch, or other components. The transmitter 710 also includes a controller 704. The controller 704 can be configured to control the angle of the EM wave transmitted by the transmitting circuit 702. For example, as illustrated, instead of directing the EM wave in the horizontal direction, the transmitter 710 directs the EM wave at an angle θ away from the horizontal direction. The angle θ can be adjusted by the controller 704. In some implementations, the controller 704 can include one or more phase shifters. In some implementations, the controller 704 can be implemented as part of the transmitting circuit 702.

The receiver 720 includes an electronic circuit that is configured to receive EM waves that are reflected from the sample 730 or penetrate through the sample 730. In the illustrated example, the receiver 720 includes a printed circuit board (PCB) 722. The PCB 722 includes a sensor array including multiple sensor 724. Each of the sensors 724 represents an electronic circuit unit that detects the intensity of the received EM wave. As shown in FIG. 7A, the sensors 424 can be organized in a 2D formation. In one example, the 2D formation can include 64 rows×64 columns. In this example, the receiver 720 can generate 64×64 received intensity values based on detected EM waves by each of the sensors 724. As discussed previously, these intensity values form an ESR image, where each intensity value represent a pixel on the ESR image. The receiver 720 can transmit the ESR image to the master device for analysis. In some cases, the receiver 720 can include an on-board memory that stores the ESR images and transmit multiple ESR images in a batch.

In operation, the transmitter 710 generates the EM wave that is radiated onto the sample 730. The sensors 724 on the receiver 720 sense the EM wave that penetrates the sample 730 and generates the ESR images accordingly.

FIG. 7B illustrates an example irradiation operation in a reflection configuration, according to an implementation. Instead of placing the sample 730 between the transmitter 710 and the receiver 720, the sample 730 is placed on the same side of the transmitter 710 and the receiver 720. In this scenario, the EM waves generated by the transmitter 710 are reflected from the sample 730, and the receiver 720 can generate ESR images based on the reflected EM waves.

Figure 8:
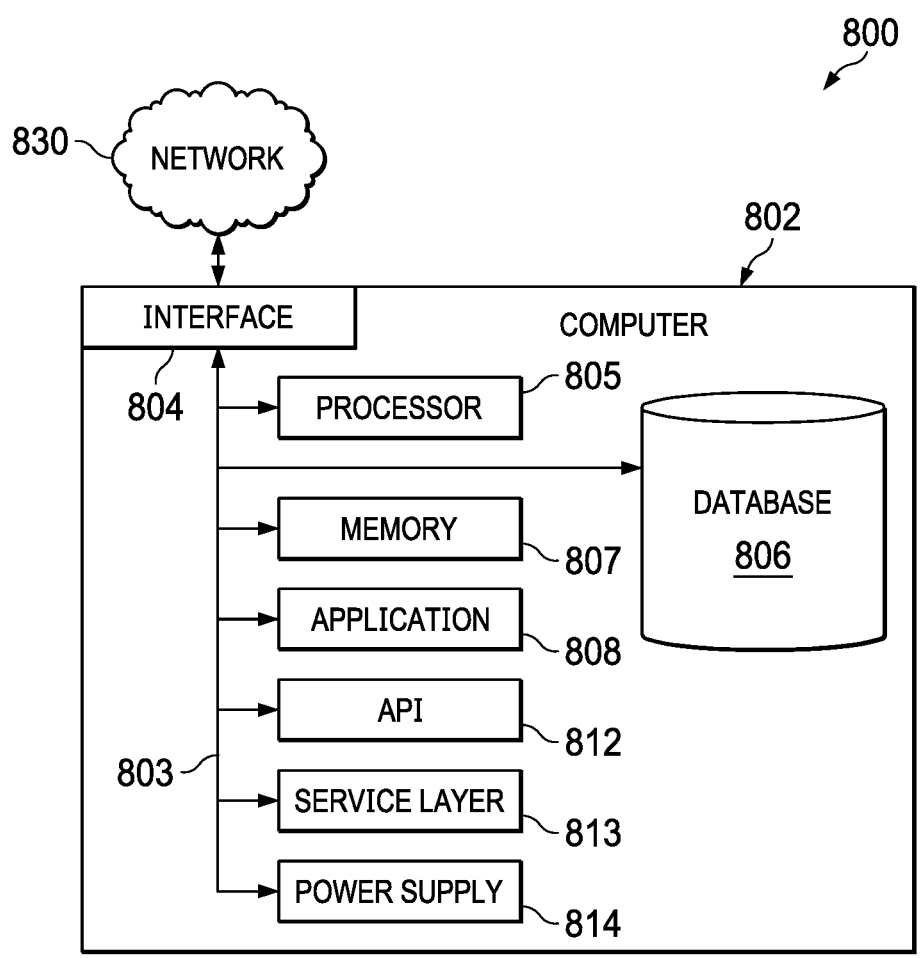
FIG. 8 is a block diagram of an example computer system used to provide computational functionalities associated with described algorithms, methods, functions, processes, flows, and procedures, as described in the instant disclosure, according to an implementation.

FIG. 8 is a block diagram of an example computer system 800 used to provide computational functionalities associated with described algorithms, methods, functions, processes, flows, and procedures, as described in the instant disclosure, according to an implementation. The computer system 800, or more than one computer system 800, can be used to implement the master device that receives the ESR images from the in-situ ESR scanner and determines source rock potentials as described previously. The computer system 800, or more than one computer system 800, can also be used to send commands to the in-situ ESR scanner to control the operations of the in-situe ESR scanner.

The illustrated computer 802 is intended to encompass any computing device such as a server, desktop computer, laptop/notebook computer, wireless data port, smart phone, personal data assistant (PDA), tablet computing device, one or more processors within these devices, or any other suitable processing device, including physical or virtual instances (or both) of the computing device. Additionally, the computer 802 may comprise a computer that includes an input device, such as a keypad, keyboard, touch screen, or other device that can accept user information, and an output device that conveys information associated with the operation of the computer 802, including digital data, visual, or audio information (or a combination of information), or a graphical user interface (GUI).

The computer 802 can serve in a role as a client, network component, a server, a database or other persistency, or any other component (or a combination of roles) of a computer system for performing the subject matter described in the instant disclosure. The illustrated computer 802 is communicably coupled with a network 830. In some implementations, one or more components of the computer 802 may be configured to operate within environments, including cloud-computing-based, local, global, or other environment (or a combination of environments).

At a high level, the computer 802 is an electronic computing device operable to receive, transmit, process, store, or manage data and information associated with the described subject matter. According to some implementations, the computer 802 may also include, or be communicably coupled with, an application server, e-mail server, web server, caching server, streaming data server, or other server (or a combination of servers).

The computer 802 can receive requests over network 830 from a client application (for example, executing on another computer 802) and respond to the received requests by processing the received requests using an appropriate software application(s). In addition, requests may also be sent to the computer 802 from internal users (for example, from a command console or by other appropriate access methods), external or third-parties, other automated applications, as well as any other appropriate entities, individuals, systems, or computers.

Each of the components of the computer 802 can communicate using a system bus 803. In some implementations, any or all of the components of the computer 802, hardware or software (or a combination of both hardware and software), may interface with each other or the interface 804 (or a combination of both), over the system bus 803 using an application programming interface (API) 812 or a service layer 813 (or a combination of the API 812 and service layer 813). The API 812 may include specifications for routines, data structures, and object classes. The API 812 may be either computer-language independent or dependent and may refer to a complete interface, a single function, or even a set of APIs. The service layer 813 provides software services to the computer 802 or other components (whether or not illustrated) that are communicably coupled to the computer 802. The functionality of the computer 802 may be accessible for all service consumers using this service layer. Software services, such as those provided by the service layer 813, provide reusable, defined functionalities through a defined interface. For example, the interface may be software written in JAVA, C++, or other suitable language providing data in extensible markup language (XML) format or other suitable format. While illustrated as an integrated component of the computer 802, alternative implementations may illustrate the API 812 or the service layer 813 as stand-alone components in relation to other components of the computer 802 or other components (whether or not illustrated) that are communicably coupled to the computer 802. Moreover, any or all parts of the API 812 or the service layer 813 may be implemented as child or sub-modules of another software module, enterprise application, or hardware module without departing from the scope of this disclosure.

The computer 802 includes an interface 804. Although illustrated as a single interface 804 in FIG. 8, two or more interfaces 804 may be used according to particular needs, desires, or particular implementations of the computer 802.

The interface 804 is used by the computer 802 for communicating with other systems that are connected to the network 830 (whether illustrated or not) in a distributed environment. Generally, the interface 804 comprises logic encoded in software or hardware (or a combination of software and hardware) and is operable to communicate with the network 830. More specifically, the interface 804 may comprise software supporting one or more communication protocols associated with communications such that the network 830 or interface's hardware is operable to communicate physical signals within and outside of the illustrated computer 802. For example, the interface 804 can be used to receive ESR images from the in-situ ESR scanner, transmit operating command to the in-situ ESR scanner, or a combination thereof.

The computer 802 includes a processor 805. Although illustrated as a single processor 805 in FIG. 8, two or more processors may be used according to particular needs, desires, or particular implementations of the computer 802. Generally, the processor 805 executes instructions and manipulates data to perform the operations of the computer 802 and any algorithms, methods, functions, processes, flows, and procedures as described in the instant disclosure.

The computer 802 also includes a database 806 that can hold data for the computer 802 or other components (or a combination of both) that can be connected to the network 830 (whether illustrated or not). For example, the database 806 can store spin concentration levels of known samples with known maturity levels that can be used to compare the ESR images received from the in-situ ESR scanner. The database 806 can be an in-memory, conventional, or other type of database storing data consistent with this disclosure. In some implementations, database 806 can be a combination of two or more different database types (for example, a hybrid in-memory and conventional database) according to particular needs, desires, or particular implementations of the computer 802 and the described functionality. Although illustrated as a single database 806 in FIG. 8, two or more databases (of the same or combination of types) can be used according to particular needs, desires, or particular implementations of the computer 802 and the described functionality. While database 806 is illustrated as an integral component of the computer 802, in alternative implementations, database 806 can be external to the computer 802.

The computer 802 also includes a memory 807 that can hold data for the computer 802 or other components (or a combination of both) that can be connected to the network 830 (whether illustrated or not). For example, memory 807 can be random access memory (RAM), read-only memory (ROM), optical, magnetic, and the like, storing data consistent with this disclosure. In some implementations, memory 807 can be a combination of two or more different types of memory (for example, a combination of RAM and magnetic storage) according to particular needs, desires, or particular implementations of the computer 802 and the described functionality. Although illustrated as a single memory 807 in FIG. 8, two or more memories 807 (of the same or combination of types) can be used according to particular needs, desires, or particular implementations of the computer 802 and the described functionality. While memory 807 is illustrated as an integral component of the computer 802, in alternative implementations, memory 807 can be external to the computer 802.

The application 808 is an algorithmic software engine providing functionality according to particular needs, desires, or particular implementations of the computer 802, particularly with respect to functionality described in this disclosure. For example, application 808 can serve as one or more components, modules, or applications. Further, although illustrated as a single application 808, the application 808 may be implemented as multiple applications 808 on the computer 802. In addition, although illustrated as integral to the computer 802, in alternative implementations, the application 808 can be external to the computer 802.

The computer 802 can also include a power supply 814. The power supply 814 can include a rechargeable or non-rechargeable battery that can be configured to be either user- or non-user-replaceable. In some implementations, the power supply 814 can include power-conversion or management circuits (including recharging, standby, or other power management functionality). In some implementations, the power-supply 814 can include a power plug to allow the computer 802 to be plugged into a wall socket or other power source to, for example, power the computer 802 or recharge a rechargeable battery.

There may be any number of computers 802 associated with, or external to, a computer system containing computer 802, each computer 802 communicating over network 830. Further, the term "client," "user," and other appropriate terminology may be used interchangeably, as appropriate, without departing from the scope of this disclosure. Moreover, this disclosure contemplates that many users may use one computer 802, or that one user may use multiple computers 802.

Described implementations of the subject matter can include one or more features, alone or in combination.

For example, in a first implementation, a method for determining source rock potential in a subterranean region of a hydrocarbon reservoir includes: receiving, an electron spin resonance (ESR) image from an in-situ ESR scanner that is attached to a wellbore at a first subterranean location, wherein the wellbore extends into the subterranean region of the hydrocarbon reservoir; determining, a spin concentration level of a source rock in the first subterranean location based on the ESR image; and determining, the source rock potential at the first subterranean location based on the determined spin concentration level.

The foregoing and other described implementations can each, optionally, include one or more of the following features:

A first feature, combinable with any of the following features, wherein the in-situ ESR scanner comprises a transmitter that is attached to the wellbore at the first subterranean location.

A second feature, combinable with any of the previous and following features, wherein the transmitter comprises transistors that are constructed radio frequency complementary metal-oxide-semiconductor (RFCMOS), silicon-germanium (SiGe), indium phosphide (InP), or gallium arsenide (GaAs).

A third feature, combinable with any of the previous and following features, wherein the in-situ ESR scanner comprises a receiver that is attached to the wellbore at the first subterranean location.

A fourth feature, combinable with any of the previous and following features, wherein the receiver comprises sensors constructed using radio frequency complementary metal-oxide-semiconductor (RFCMOS), silicon-germanium (SiGe), indium phosphide (InP), or gallium arsenide (GaAs).

A fifth feature, combinable with any of the previous and following features, wherein the ESR image is generated by irradiating microwaves at the first subterranean location.

A sixth feature, combinable with any of the previous and following features, wherein the microwaves have frequencies in L band.

A seventh feature, combinable with any of the previous and following features, further comprising: receiving, a second ESR image from a second in-situ ESR scanner that is attached to the wellbore at the second subterranean location; and determining, the source rock potential at the second subterranean location based on the second ESR image.

An eighth feature, combinable with any of the previous and following features, wherein both the first subterranean location and the second subterranean location are located on a horizontal portion of the wellbore.

A ninth feature, combinable with any of the previous features, further comprising: receiving an identification of the in-situ ESR scanner that transmits the ESR image.

In a second implementation, an in-situ electron spin resonance (ESR) scanner includes: a transmitter configured to irradiate microwaves to a source rock sample in a first subterranean location of a hydrocarbon reservoir; a receiver configured to generate ESR images based on the microwaves that are reflected from the source rock sample or penetrated through the source rock sample; a magnet configured to generate a magnetic field for ESR measurement of the source rock sample; and a communication interface configured to transmit the ESR image to a surface of the reservoir.

The foregoing and other described implementations can each, optionally, include one or more of the following features:

A first feature, combinable with any of the following features, wherein the transmitter comprises transistors that are constructed using radio frequency complementary metal-oxide-semiconductor (RFCMOS), silicon-germanium (SiGe), indium phosphide (InP), or gallium arsenide (GaAs).

A second feature, combinable with any of the previous and following features, wherein the receiver comprises transistors that are constructed using radio frequency complementary metal-oxide-semiconductor (RFCMOS), silicon-germanium (SiGe), indium phosphide (InP), or gallium arsenide (GaAs).

A third feature, combinable with any of the previous and following features, wherein the microwaves have frequencies in L band.

A fourth feature, combinable with any of the previous features, wherein the communication interface is further configured to transmit an identification of the in-situ ESR scanner.

In a third implementation, a method for scanning a source rock sample in a subterranean region of a hydrocarbon reservoir includes: generating, by an in-situ electron spin resonance (ESR) scanner, a magnetic field for the source rock sample at a first subterranean location; irradiating, by the ESR scanner, microwaves to the source rock sample at a first subterranean location; generating an ESR image based on the microwaves that are reflected from the source rock sample or penetrated through the source rock sample; and transmitting the ESR image to a surface of the reservoir.

The foregoing and other described implementations can each, optionally, include one or more of the following features:

A first feature, combinable with any of the following features, wherein the in-situ ESR scanner comprises a transmitter that is attached to the wellbore at the first subterranean location.

A second feature, combinable with any of the previous and following features, wherein the transmitter comprises transistors that are constructed radio frequency complementary metal-oxide-semiconductor (RFCMOS), silicon-germanium (SiGe), indium phosphide (InP), or gallium arsenide (GaAs).

A third feature, combinable with any of the previous and following features, wherein the in-situ ESR scanner comprises a receiver that is attached to the wellbore at the first subterranean location.

A fourth feature, combinable with any of the previous features, wherein the receiver comprises sensors constructed using radio frequency complementary metal-oxide-semiconductor (RFCMOS), silicon-germanium (SiGe), indium phosphide (InP), or gallium arsenide (GaAs).

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Implementations of the subject matter described in this specification can be implemented as one or more computer programs, that is, one or more modules of computer program instructions encoded on a tangible, non transitory computer-storage medium for execution by, or to control the operation of, data processing apparatus. Alternatively or in addition, the program instructions can be encoded on an artificially generated propagated signal, for example, a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of one or more of them.

The terms "data processing apparatus," "computer," or "electronic computer device" (or equivalent as understood by one of ordinary skill in the art) refer to data processing hardware and encompass all kinds of apparatus, devices, and machines for processing data, including by way of example, a programmable processor, a computer, or multiple processors or computers. The apparatus can also be, or further include, special purpose logic circuitry, for example, a central processing unit (CPU), a FPGA (field programmable gate array), or an ASIC (application specific integrated circuit). In some implementations, the data processing apparatus or special purpose logic circuitry may be hardware-based or software-based. The apparatus can optionally include code that creates an execution environment for computer programs, for example, code that constitutes processor firmware, a protocol stack, a database management system, an operating system, or a combination of one or more of them. The present disclosure contemplates the use of data processing apparatuses with or without conventional operating systems, for example LINUX, UNIX, WINDOWS, MAC OS, ANDROID, or IOS.

A computer program, which may also be referred to or described as a program, software, a software application, a module, a software module, a script, or code can be written in any form of programming language, including compiled or interpreted languages, or declarative or procedural languages, and it can be deployed in any form, including as a stand alone program or as a module, component, subroutine, or other unit suitable for use in a computing environment. A computer program may, but need not, correspond to a file in a file system. A program can be stored in a portion of a file that holds other programs or data, for example, one or more scripts stored in a markup language document, in a single file dedicated to the program in question, or in multiple coordinated files, for example, files that store one or more modules, sub programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third-party services, components, or libraries. Conversely, the features and functionality of various components can be combined into single components, as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, for example, a CPU, an FPGA, or an ASIC.

Computers suitable for the execution of a computer program can be based on general or special purpose microprocessors, both, or any other kind of CPU. Generally, a CPU will receive instructions and data from a read only memory (ROM) or a random access memory (RAM) or both. The essential elements of a computer are a CPU for performing or executing instructions and one or more memory devices for storing instructions and data. Generally, a computer will also include, or be operatively coupled to, receive data from or transfer data to, or both, one or more mass storage devices for storing data, for example, magnetic, magneto optical disks, or optical disks. However, a computer need not have such devices. Moreover, a computer can be embedded in another device, for example, a mobile telephone, a personal digital assistant (PDA), a mobile audio or video player, a game console, a global positioning system (GPS) receiver, or a portable storage device, for example, a universal serial bus (USB) flash drive, to name just a few.

Computer readable media (transitory or non-transitory, as appropriate) suitable for storing computer program instructions and data include all forms of non volatile memory, media and memory devices, including by way of example semiconductor memory devices, for example, erasable programmable read-only memory (EPROM), electrically erasable programmable read-only memory (EEPROM), and flash memory devices; magnetic disks, for example, internal hard disks or removable disks; magneto optical disks; and CD ROM, DVD+/−R, DVD-RAM, and DVD-ROM disks. The memory may store various objects or data, including caches, classes, frameworks, applications, backup data, jobs, web pages, web page templates, database tables, repositories storing business or dynamic information, and any other appropriate information including any parameters, variables, algorithms, instructions, rules, constraints, or references thereto. Additionally, the memory may include any other appropriate data, such as logs, policies, security or access data, or reporting files. The processor and the memory can be supplemented by, or incorporated in, special purpose logic circuitry.

To provide for interaction with a user, implementations of the subject matter described in this specification can be implemented on a computer having a display device, for example, a CRT (cathode ray tube), LCD (liquid crystal display), LED (Light Emitting Diode), or plasma monitor, for displaying information to the user and a keyboard and a pointing device, for example, a mouse, trackball, or trackpad by which the user can provide input to the computer. Input may also be provided to the computer using a touchscreen, such as a tablet computer surface with pressure sensitivity or a multi-touch screen using capacitive or electric sensing. Other kinds of devices can be used to provide for interaction with a user as well; for example, feedback provided to the user can be any form of sensory feedback, for example, visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or "GUI," may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons operable by the business suite user. These UI elements may be related to or represent the functions of the web browser.

Implementations of the subject matter described in this specification can be implemented in a computing system that includes a back end component, for example, as a data server, or that includes a middleware component, for example, an application server, or that includes a front-end component, for example, a client computer having a graphical user interface or a Web browser through which a user can interact with an implementation of the subject matter described in this specification, or any combination of one or more such back end, middleware, or front end components. The components of the system can be interconnected by any form or medium of wireline or wireless digital data communication, for example, a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) using, for example, 802.11 a/b/g/n or 802.20, and all or a portion of the Internet. The network may communicate with, for example, Internet Protocol (IP) packets, Frame Relay frames, Asynchronous Transfer Mode (ATM) cells, voice, video, data, or other suitable information between network addresses.

The computing system can include clients and servers. A client and server are generally remote from each other and typically interact through a communication network. The relationship of client and server arises by virtue of computer programs running on the respective computers and having a client-server relationship to each other.

In some implementations, any or all of the components of the computing system, both hardware or software, may interface with each other or the interface using an application programming interface (API) or a service layer. The API may include specifications for routines, data structures, and object classes. The API may be either computer language independent or dependent and refer to a complete interface, a single function, or even a set of APIs. The service layer provides software services to the computing system. The functionality of the various components of the computing system may be accessible for all service consumers via this service layer. Software services provide reusable, defined business functionalities through a defined interface. For example, the interface may be software written in JAVA, C++, or other suitable language providing data in extensible markup language (XML) format or other suitable format. The API or service layer may be an integral or a stand-alone component in relation to other components of the computing system. Moreover, any or all parts of the service layer may be implemented as child or sub-modules of another software module, enterprise application, or hardware module without departing from the scope of this disclosure.

While this specification contains many specific implementation details, these should not be construed as limitations on the scope of any disclosure or on the scope of what may be claimed, but rather as descriptions of features that may be specific to particular implementations of particular disclosures. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described as acting in certain combinations and even initially claimed as such, one or more features from a claimed combination can in some cases be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking and parallel processing may be advantageous.

Moreover, the separation or integration of various system modules and components in the implementations described previously should not be understood as requiring such separation or integration in all implementations, and it should be understood that the described program components and systems can generally be integrated together in a single software product or packaged into multiple software products.

Accordingly, the previous description of example implementations does not define or constrain this disclosure. Other changes, substitutions, and alterations are also possible without departing from the spirit and scope of this disclosure.

What is claimed is:

1. A method for determining source rock potential in a subterranean region of a hydrocarbon reservoir, comprising:
    receiving, an electron spin resonance (ESR) image from an in-situ ESR scanner that is attached to a wellbore at a first subterranean location, wherein the wellbore extends into the subterranean region of the hydrocarbon reservoir;
    determining, a spin concentration level of a source rock in the first subterranean location based on the ESR image, wherein the spin concentration level indicates a concentration level of free radicals in kerogen; and
    determining, the source rock potential at the first subterranean location based on the determined spin concentration level and a comparison of concentration levels between carbon-13 and carbon-12.

2. The method of claim 1, wherein the in-situ ESR scanner comprises a transmitter that is attached to the wellbore at the first subterranean location.

3. The method of claim 2, wherein the transmitter comprises transistors that are constructed using radio frequency complementary metal-oxide-semiconductor (RFCMOS), silicon-germanium (SiGe), indium phosphide (InP), or gallium arsenide (GaAs).

4. The method of claim 1, wherein the in-situ ESR scanner comprises a receiver that is attached to the wellbore at the first subterranean location.

5. The method of claim 4, wherein the receiver comprises sensors constructed using radio frequency complementary metal-oxide-semiconductor (RFCMOS), silicon-germanium (SiGe), indium phosphide (InP), or gallium arsenide (GaAs).

6. The method of claim 1, wherein the ESR image is generated by irradiating microwaves at the first subterranean location.

7. The method of claim 6, wherein the microwaves have frequencies in an L band.

8. The method of claim 1, further comprising:
    receiving, a second ESR image from a second in-situ ESR scanner that is attached to the wellbore at a second subterranean location; and
    determining, the source rock potential at the second subterranean location based on the second ESR image.

9. The method of claim 8, wherein both the first subterranean location and the second subterranean location are located on a horizontal portion of the wellbore.

10. The method of claim 1, further comprising: receiving an identification of the in-situ ESR scanner that transmits the ESR image.

11. An electron spin resonance (ESR) system, comprising:
    an in-situ ESR scanner, comprising:
        a transmitter configured to irradiate microwaves to a source rock sample in a first subterranean location of a hydrocarbon reservoir;
        a receiver configured to generate ESR images based on the microwaves that are reflected from the source rock sample or penetrated through the source rock sample, wherein the ESR image indicates a concentration level of free radicals in kerogen;
        a magnet configured to generate a magnetic field for ESR measurement of the source rock sample; and
        a communication interface configured to transmit the ESR image to a surface of the reservoir; and
    an analyzer configured to determine a source rock potential at the first subterranean location based on the concentration level of free radicals and a comparison of concentration levels between carbon-13 and carbon-12.

12. The in-situ ESR scanner of claim 11, wherein the transmitter comprises transistors that are constructed using radio frequency complementary metal-oxide-semiconductor (RFCMOS), silicon-germanium (SiGe), indium phosphide (InP), or gallium arsenide (GaAs).

13. The in-situ ESR scanner of claim 11, wherein the receiver comprises transistors that are constructed using radio frequency complementary metal-oxide-semiconductor (RFCMOS), silicon-germanium (SiGe), indium phosphide (InP), or gallium arsenide (GaAs).

14. The in-situ ESR scanner of claim 11, wherein the microwaves have frequencies in an L band.

15. The in-situ ESR scanner of claim 11, wherein the communication interface is further configured to transmit an identification of the in-situ ESR scanner.

16. A method for scanning a source rock sample in a subterranean region of a hydrocarbon reservoir, comprising:
generating, by an in-situ electron spin resonance (ESR) scanner, a magnetic field for the source rock sample at a first subterranean location;
irradiating, by the ESR scanner, microwaves to the source rock sample at the first subterranean location;
generating an ESR image based on the microwaves that are reflected from the source rock sample or penetrated through the source rock sample, wherein the ESR image indicates a concentration level of free radicals in kerogen; and
transmitting the ESR image to a surface of the reservoir, wherein the ESR image is used to determine a source rock potential at the first subterranean location based on the concentration level of free radicals and a comparison of concentration levels between carbon-13 and carbon-12.

17. The method of claim 16, wherein the in-situ ESR scanner comprises a transmitter that is attached to a wellbore at the first subterranean location.

18. The method of claim 17, wherein the transmitter comprises transistors that are constructed using radio frequency complementary metal-oxide-semiconductor (RFCMOS), silicon-germanium (SiGe), indium phosphide (InP), or gallium arsenide (GaAs).

19. The method of claim 16, wherein the in-situ ESR scanner comprises a receiver that is attached to a wellbore at the first subterranean location.

20. The method of claim 19, wherein the receiver comprises sensors constructed using radio frequency complementary metal-oxide-semiconductor (RFCMOS), silicon-germanium (SiGe), indium phosphide (InP), or gallium arsenide (GaAs).

* * * * *